(12) United States Patent
Potyen et al.

(10) Patent No.: US 7,767,833 B2
(45) Date of Patent: Aug. 3, 2010

(54) STABILIZED BORANE-TETRAHYDROFURAN COMPLEX

(75) Inventors: Mark C. Potyen, Sheboygan, WI (US); Kanth V. B. Josyula, Germantown, WI (US); Peng Gao, Mequon, WI (US); Christopher Dudley Hewitt, Shorewood, WI (US)

(73) Assignee: Sigma-Aldrich Co., St. Louis, MO (US)

( * ) Notice: Subject to any disclaimer, the term of this patent is extended or adjusted under 35 U.S.C. 154(b) by 630 days.

(21) Appl. No.: 11/573,608

(22) PCT Filed: Aug. 8, 2005

(86) PCT No.: PCT/US2005/028271

§ 371 (c)(1),
(2), (4) Date: Mar. 20, 2008

(87) PCT Pub. No.: WO2006/020639

PCT Pub. Date: Feb. 23, 2006

(65) Prior Publication Data

US 2008/0275255 A1 Nov. 6, 2008

Related U.S. Application Data

(60) Provisional application No. 60/600,868, filed on Aug. 12, 2004.

(51) Int. Cl.
*C07F 5/02* (2006.01)
(52) U.S. Cl. .................................. 549/213; 252/182.29
(58) Field of Classification Search ................... 549/213
See application file for complete search history.

(56) References Cited

U.S. PATENT DOCUMENTS

| | | | |
|---|---|---|---|
| 3,609,191 A | 9/1971 | Wade | |
| 3,634,277 A | 1/1972 | Brown | |
| 3,882,037 A | 5/1975 | Brown | |
| 4,008,282 A | 2/1977 | Townsend | |
| 4,029,712 A | 6/1977 | Tsuchihashi | |
| 4,390,729 A | 6/1983 | Oswald | |
| 4,503,178 A | 3/1985 | Green | |
| 5,100,854 A | 3/1992 | Maeda et al. | |
| 5,250,736 A | 10/1993 | Micklethwaite et al. | |
| 5,260,485 A | 11/1993 | Calbick et al. | |
| 5,466,798 A | 11/1995 | Singaram et al. | |
| 5,481,038 A | 1/1996 | Brown | |
| 5,504,240 A | 4/1996 | Brown | |
| 5,543,569 A | 8/1996 | Brown | |
| 5,567,849 A | 10/1996 | Brown | |
| 5,663,419 A | 9/1997 | Sugiya et al. | |
| 6,048,985 A | 4/2000 | Burkhardt et al. | |
| 6,218,585 B1 | 4/2001 | Matos et al. | |
| 6,248,885 B1 | 6/2001 | Brown | |
| 6,545,183 B1 | 4/2003 | Berens | |
| 6,610,894 B2 | 8/2003 | Matos et al. | |

OTHER PUBLICATIONS

M. Follet, "Use of Complexes of Diborane and Organoboranes on a Laboratory and Industrial Scale", Chemistry and Industry Journal, 1986, pp. 123-128.
K. Smith, "Advances in Organometallic Chemistry—Prospects for Industry", Chemistry and Industry Journal, 1987, pp. 603-611.
Clinton F. Lane, "Reduction of Organic Compounds with Diborane", Chemical Reviews, 1976, pp. 773-799.
Herbert C. Brown, Manoj C. Desai, Prabhakar K. Jadhav, "Diisopinocapmheylborane of High Optical Purity. Improved Preparation and Asymmetric Hydroboration of Representative Cis-Disubstituted Alkenes", Journal of Organic Chemistry, 1982, pp. 5065-5069, vol. 47.
Herbert C. Brown, Peter Heim, Nung Min Yoon, "Reaction of Diborane in Tetrahydrofuran with Selected Organic Compounds Containing Representative Functional Groups", Journal of American Chemical Society, pp. 1637-1646, vol. 92, (1970).
International Preliminary Report on Patentability for PCT/US2005/028271 dated Feb. 22, 2007.

*Primary Examiner*—Bernard Dentz
(74) *Attorney, Agent, or Firm*—Senniger Powers LLP; Jill Rogers-Manning

(57) ABSTRACT

A stabilized borane-tetrahydrofuran complex is disclosed. Also disclosed are processes for the preparation of the borane-tetrahydrofuran complex and methods of storing and transporting the prepared complex. The borane-tetrahydrofuran complexes exhibit enhanced shelf life and increased self-accelerated decomposition temperatures.

24 Claims, 4 Drawing Sheets

STABILIZED BORANE-TETRAHYDROFURAN COMPLEX

BACKGROUND OF THE INVENTION

Diborane ($B_2H_6$) is a versatile reagent with broad applications in organic and inorganic syntheses. Because diborane is a pyrophoric gas having a flash point of about −90° C. and an autoignition temperature of about 38° C. to 51° C., borane complexes with Lewis bases are typically used instead, as they are more convenient to handle. Numerous examples of these borane complexes for use in the synthesis of pharmaceuticals and other industrial applications are well known in the art. Borane-tetrahydrofuran complex (sometimes referred to as ("BTHF" or "BTHF complex") is one of the more widely used borane-Lewis base complexes for synthetic applications, such as hydroboration of carbon-carbon double and triple bonds, and reduction of various functional groups.

Problematically, BTHF solutions having a concentration in excess of about 2.0 moles per liter readily release diborane. In part because of instability issues, therefore, BTHF complex has been commercially available only as low concentration solutions for a number of years. Under the United States Department of Transportation ("DOT") regulations, transportation of a package containing a material which is likely to decompose with a self-accelerated decomposition temperature (SADT) of 50° C. or less with an evolution of a dangerous quantity of heat or gas when decomposing is prohibited unless the material is stabilized or inhibited in a manner to preclude such evolution Because of the intrinsic instability and low autoignition temperature, BTHF solutions known in the art having a BTHF concentration in excess of about 1 mole per liter generally cannot meet the SADT mandated by the DOT. Aside from resulting in unacceptable SADT temperatures, diborane exhibits high vapor pressure at room temperature resulting in overpressurization of storage containers. Moreover, diborane can attack the tetrahydrofuran ("THF") cyclic ether linkage causing ring opening thereby resulting in less pure BTHF and concomitant heat generation and container pressurization.

Another problem associated with BTHF complexes is short shelf life, especially at temperatures at or above normal room temperature of about 25° C. BTHF complexes can decompose during shipping or in storage if they are not stabilized properly, or are shipped at elevated temperature. For instance, as described in U.S. Pat. No. 6,048,985 to Burkhardt et al., the assay of a 2 molar solution of BTHF stored at room temperature (i.e., 20° C. to 25° C.) dropped from about 98% to about 16% over a period of 110 days.

In U.S. Pat. No. 3,634,277, Brown disclosed stabilizing BTHF from ring-opening ether cleavage of the tetrahydrofuran ("THF"), to some extent, with borohydride. In each of Brown's examples, however, BTHF solutions having concentrations of 1.5 to 2.0 M BTHF experienced significant decomposition of the BTHF in shelf-life/stability experiments conducted at ambient temperature for eight weeks. In addition, stabilization of BTHF with sodium borohydride does not significantly increase the SADT temperature to 50° C. or above. Also, $NaB_2H_7$, a possible by product from such stabilized solutions formed by the reaction of $NaBH_4$ with borane, is relatively insoluble in THF and may drop out of solution as a solid precipitate thereby causing storage and material transfer problems. This is true for BTHF prepared by in situ methods or by passing highly pure diborane gas into the THF.

In the interest of conservation of resources and efficient use of reactor vessels, one would like to conduct reactions at the highest concentration possible for a particular reaction. In that regard, the low concentration of the BTHF leads to low reactor loading and inefficient use of equipment. There are several reports in the literature, however, that solutions of BTHF of greater than 1 mole per liter are unavailable as a result of the instability of such solutions. See, for example, H. C. Brown, P. Heim, N. M. Yoon JACS, 92, 1637-1646 (1970); C. F. Lane Chem. Rev., 76, 773-799 (1976); H. C. Brown, M. C. Desai, P. K. Jadhav JOC, 47, 5065-5069 (1982); M. Follet Chem. And Industry., 123-128; and K. Smith, Chem. and Industry 1987, 603-611 (1986).

Borane reagents other than BTHF complex are available in more concentrated form, but each has inherent disadvantages. For example, sulfide boranes are highly concentrated but suffer from noxious odors and amine-boranes known in the art are less reactive than BTHF. In addition, such complexing agents (amine or sulfide) are often difficult to remove from the desired product.

SUMMARY OF THE INVENTION

Among the various aspects of the present invention are stabilized borane-tetrahydrofuran complex solutions, processes for their preparation, and methods of storing and transporting those solutions.

Briefly, therefore, the present invention is directed to a solution containing a borane-tetrahydrofuran complex, tetrahydrofuran and a stabilizer. The stabilizer is selected from the group consisting of amines, sulfides, phosphines, aminoborohydrides, borates, and combinations thereof. The concentration of the borane-tetrahydrofuran complex in the solution is at least about 0.5 moles per liter, and the molar ratio of the borane-tetrahydrofuran complex to the stabilizer is at least 10:1.

The present invention is further directed to a process for the preparation of a stabilized borane-tetrahydrofuran complex in a solution containing tetrahydrofuran. The process comprises forming a solution containing borane-tetrahydrofuran complex and a solvent system comprising tetrahydrofuran, the concentration of the borane-tetrahydrofuran complex in the solution being at least about 0.5 moles per liter. A stabilizer is combined with the solvent system in a molar ratio of the borane-tetrahydrofuran complex to the stabilizer in the solution of at least 10:1, the stabilizer being selected from the group consisting of amines, sulfides, phosphines, aminoborohydrides, borates, and combinations thereof. The process steps can be carried out in any order.

The present invention is further directed to a method of storing and transporting a solution containing at least about 0.5 moles per liter of a borane-tetrahydrofuran complex in solution in a solvent system comprising tetrahydrofuran. The solution further comprises a stabilizer selected from the group consisting of amines, sulfides, phosphines, aminoborohydrides, borates, and combinations thereof wherein the molar ratio of the borane-tetrahydrofuran complex to the stabilizer is at least 10:1. The method comprises sealing the liquid borane-tetrhydrofuran complex solution in a container having a storage volume of at least 0.10 liters and transporting the sealed container to another location. In one embodiment, the ratio of the surface area at the gas-liquid interface within the container to the volume of liquid in the container is at least about 2 cm² per liter.

The present invention is further directed to a method of storing and transporting a solution containing at least about 0.5 moles per liter of a borane-tetrahydrofuran complex in a solvent system containing tetrahydrofuran. The solution is sealed in a container having a free space occupied by a gas. The ratio of the surface area of the gas-solution interface to the volume of the solution in the sealed container is about 2 cm² per liter to about 200 cm² per liter. The sealed container can then be transported.

Other objects and features of this invention will be in part apparent and in part pointed out hereinafter.

DETAILED DESCRIPTION OF THE INVENTION

Figure 1:
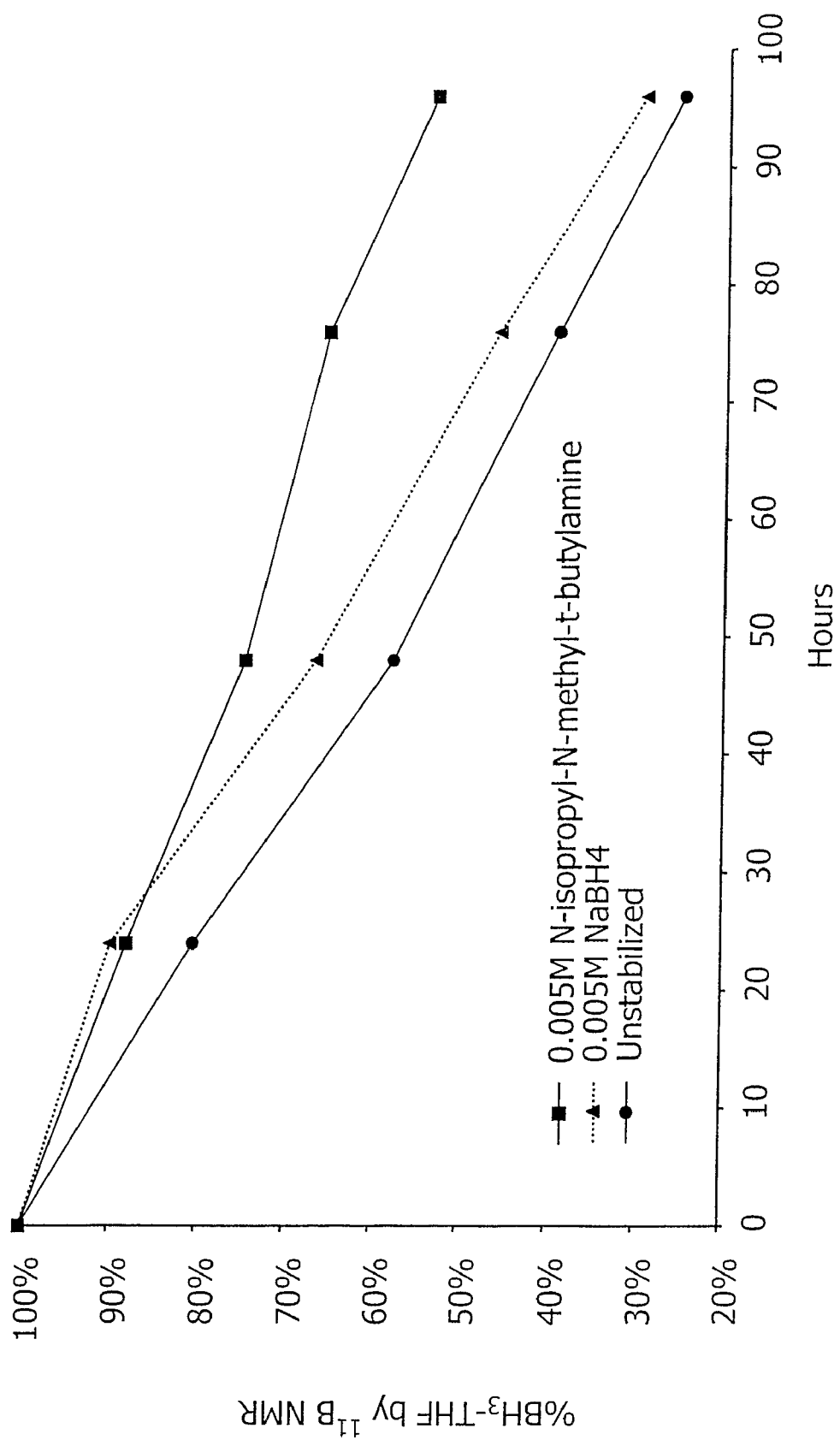
FIG. 1 is a graph of the mole percent borane-THF remaining (by ¹¹B NMR) in solution versus time in hours for unstabilized and stabilized 1 mole per liter borane-THF solutions held at a temperature of 50° C.

In accordance with the present invention, stabilized BTHF solutions having a THF concentration of at least about 0.5 molar are provided. As compared to BTHF solutions known in the art, such stabilized solutions have an increased shelf life at temperatures of at least about 5° C., an elevated SADT temperature of at least about 50° C., or both.

In general, temperature stability or SADT temperature elevation is achieved by including in the THF solution, a stabilizer selected from the group consisting of amines, sulfides, phosphines, aminoborohydrides, borates, and combinations thereof. Preferred amines include non-cyclic and cyclic secondary and tertiary amines, amine oxides, and metal amides. Preferred phosphines include the non-cyclic and cyclic secondary and tertiary forms, and phosphine oxides. Preferred sulfides include the secondary non-cyclic and cyclic forms, and sulfoxides. Preferred borates include boric acid esters and tetralkoxyborate salts.

In particular, such stabilizers offer particular utility in stabilizing THF solutions containing at least 0.5 moles per liter of dissolved BTHF. Typically, the stabilized THF solution has a dissolved BTHF concentration not in excess of 2.5M. In one preferred embodiment, the stabilized solution has a dissolved BTHF concentration of about 1M to about 2.5M; in another preferred embodiment, the stabilized solution has a dissolved BTHF concentration of about 1M to about 2M; in another preferred embodiment, the stabilized solution has a dissolved BTHF concentration of about 1M to about 1.5M; in another preferred embodiment, the stabilized solution has a dissolved BTHF concentration of about 1.5M to about 2.5M; in yet another preferred embodiment, the stabilized solution has a dissolved BTHF concentration of about 1.5M to about 2M; and in yet another preferred embodiment, the stabilized solution has a dissolved BTHF concentration of about 2M to about 2.5M.

Without being bound to any particular theory, it has been proposed that the stabilizers scavenge diborane through the formation of a stabilizer-diborane complex having a dynamic equilibrium in THF solution sufficient to deliver borane back to THF and reform BTHF. Stabilization can be represented by the following reaction scheme:

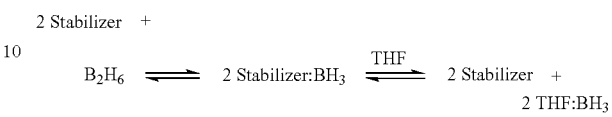

Regardless of mechanism, the stabilizers of the present invention yield BTHF complex solutions having a greater SADT temperature, longer shelf life at ambient temperature, or both, than stabilized BTHF solutions previously known in the art.

In general, a molar ratio excess of BTHF to stabilizer(s) in the THF solution is preferred. Preferably, the molar ratio of BTHF to stabilizer(s) is greater than about 10:1, respectively. More preferably, the molar ratio of BTHF to stabilizer(s) in the THF solution is between 10:1 and 10,000:1, respectively. In one preferred embodiment, the molar ratio of BTHF to stabilizer(s) in the THF solution is about 50:1 to about 1000:1, respectively. In another preferred embodiment, the molar ratio of BTHF to stabilizer(s) in the THF solution is between 100:1 and 500:1, respectively.

The stabilizer(s) of the present invention may be fully dissolved in the THF solution or, alternatively, immobilized onto a polymeric or other solid support, or be present within the matrix of a polymeric or other solid support. Thus, for example, when a secondary or tertiary amine is used as a stabilizer, it may be dissolved in the THF solution; alternatively, it may be immobilized onto or in a resin particle or other solid combined with the THF solution. For example, the stabilizer may be immobilized on a resin particle added to the THF solution or immobilized to the inner wall of a container holding the THF solution. Furthermore, combinations of stabilizers may be used in each of these permutations. Thus, for example, an immobilized secondary or tertiary amine may be used in combination with one or more dissolved stabilizers selected from the group consisting of secondary or tertiary amines, sulfides, phosphines, borates and aminoborohydrides. Regardless, it is generally preferred that the molar ratio of BTHF to all such stabilizer(s) in the THF solution (regardless of whether they are immobilized or dissolved) be between 10:1 and 10,000:1, respectively. In one embodiment, the stabilizer consists of only the secondary or tertiary amine; that is, the stabilizer does not additionally comprise an aminoborohydride, metal amide, sulfide, phosphine, borate, or borohydride. In another embodiment, a combination of two or more of these stabilizers is used.

In one preferred embodiment, the THF solution contains an amine BTHF stabilizer such as a non-cyclic secondary amine, tertiary-amine, amine-N-oxide, aminoborane or metal amide. Preferred non-cyclic secondary and tertiary amines are represented by chemical formula (Ia):

preferred amine-N-oxides are represented by chemical formula (Ib):

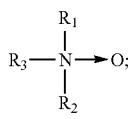

preferred aminoboranes are represented by chemical formula (Ic):

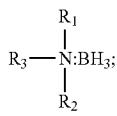

and preferred metal amides are represented by chemical formula (Id):

wherein, for tertiary amines and amine oxides, $R_1$, $R_2$ and $R_3$ are independently selected from aryl, heteroaryl, straight or branched chain alkyl, alkene or alkoxy having 1 to 8 carbon atoms, cycloalkyl having 3 to 8 carbon atoms, and tri-substituted silyl. For secondary amines and amine oxides, one of $R_1$, $R_2$ or $R_3$ as defined above is hydrogen. For metal amides, $R_1$ and $R_2$ are independently selected from aryl, heteroaryl, straight or branched chain alkyl, alkene or alkoxy having 1 to 8 carbon atoms, cycloalkyl having 3 to 8 carbon atoms, and tri-substituted silyl. $M^+$ is any suitable counterion with metals such as sodium, potassium or lithium being preferred. A preferred aryl is phenyl ($C_6H_5$). The silyl may be substituted with the groups independently selected from hydrogen, phenyl, straight or branched chain alkyl, alkene or alkoxy having 1 to 8 carbon atoms, and cycloalkyl having 3 to 8 carbon atoms. A preferred silyl is trimethylsilyl. Secondary and tertiary amines of formula (Ia) are known in the art. See for example U.S. Pat. Nos. 5,481,038, 5,543,569 and 6,248,885 to Brown, all of which are incorporated by reference.

Representative non-cyclic tertiary amine stabilizers are indicated in Table 1. Representative amine oxides can be derived from Table 1 where $R_1$, $R_2$ and $R_3$ can be any one of the listed moieties. Representative metal amides can be derived from Table 1 where $R_1$ and $R_2$ can be any one of the listed moieties. Representative non-cyclic secondary amine stabilizers can be derived from the compounds of Table 1 where any one of $R_1$, $R_2$ and $R_3$ is hydrogen instead of the listed moiety.

TABLE 1

| Stabilizer | $R_1$ | $R_2$ | $R_3$ |
|---|---|---|---|
| 1 | $C_6H_5$ | i-butyl | methyl |
| 2 | $C_6H_5$ | i-butyl | ethyl |
| 3 | $C_6H_5$ | i-butyl | i-butyl |
| 4 | $C_6H_5$ | i-butyl | n-propyl |
| 5 | $C_6H_5$ | i-propyl | methyl |
| 6 | $C_6H_5$ | i-propyl | ethyl |
| 7 | $C_6H_5$ | i-propyl | n-propyl |
| 8 | $C_6H_5$ | i-propyl | i-propyl |
| 9 | t-butyl | —$CH_2CH_2OCH_2CH_2$ | —$CH_2CH_2OCH_2CH_2$ |
| 10 | t-butyl | ethyl | ethyl |
| 11 | t-butyl | n-propyl | n-propyl |
| 12 | t-butyl | —$CH_2CH_2OCH_3$ | —$CH_2CH_2OCH_3$ |
| 13 | t-butyl | i-butyl | i-butyl |
| 14 | t-butyl | methyl | i-butyl |
| 15 | t-butyl | methyl | i-propyl |
| 16 | t-butyl | ethyl | i-butyl |
| 17 | t-butyl | n-propyl | i-butyl |
| 18 | t-butyl | ethyl | i-propyl |
| 19 | t-octal | methyl | methyl |
| 20 | t-octal | ethyl | methyl |
| 21 | t-octyl | —$CH_2CH_2OCH_2CH_2$ | —$CH_2CH_2OCH_2CH_2$ |
| 22 | t-octal | ethyl | ethyl |
| 23 | t-octal | i-butyl | methyl |
| 24 | t-octal | n-propyl | -propyl |
| 25 | i-propyl | i-propyl | i-butyl |
| 26 | i-propyl | i-propyl | methallyl |
| 27 | t-octyl | n-propyl | n-propyl |
| 28 | i-propyl | i-propyl | i-propyl |
| 29 | n-butyl | ethyl | ethyl |
| 30 | i-propyl | i-propyl | sec-butyl |

In another preferred embodiment, the secondary or tertiary amine is a six or five membered cyclic amine of chemical formulae (II) and (III), respectively:

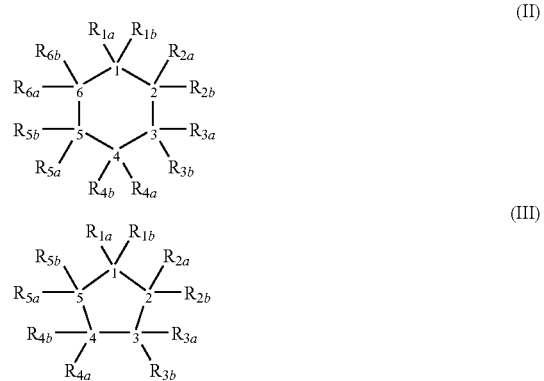

wherein, for the six-membered ring of formula (II), at least one atom and no more than three atoms at positions 1-6 are nitrogen, the ring can include an oxygen, phosphorous or sulfur heteroatom, and the remaining ring atoms are carbon. For the five-membered ring of formula (III), at least one atom and no more than three atoms at any one of positions 1-5 are nitrogen, the ring can contain an oxygen, phosphorous or sulfur heteroatom, and the remaining ring atoms are carbon. The rings of formulae (II) or (III) can be unsaturated, partially unsaturated, or completely saturated. In the case of nitrogen ring atoms, only $R_{xa}$ (where x is any one of 1-6 for rings of formula (II) and 1-5 for rings of formula (III)) is present at that atom, and where the ring is partially unsaturated or completely saturated, the nitrogen atom $R_{xa}$ substituent can represent a shared electron or electron pair. For carbon ring atoms, in the case of unsaturated rings, both $R_{xa}$ and $R_{xb}$ are present at that atom, and where the ring is partially unsaturated or completely saturated one of the carbon atom $R_{xa}$ or $R_{xb}$ substituent can represent a shared electron or electron pair.

Preferred six-membered rings include substituted or unsubstituted piperidine, piperazine, pyridine, pyrazine, pyridazine and pyrimidine. Preferred five-membered rings include substituted or unsubstituted 1H-Pyrrole, pyrrolidine, 3-pyrroline, imidazole, pyrazole, 2-pyrazoline and triazole. For rings of formula (II), $R_{1a}$ through $R_{6b}$ are independently selected from a shared electron, electron pair, hydrogen, straight or branched chain alkyl, alkene or alkoxy having 1 to 8 carbon atoms, and cycloalkyl having 3 to 8 carbon atoms. For rings of formula (III), $R_{1a}$ through $R_{5b}$ are independently selected from a shared electron, electron pair, hydrogen, straight or branched chain alkyl, alkene or alkoxy having 1 to 8 carbon atoms, and cycloalkyl having 3 to 8 carbon atoms. An example of a cyclic stabilizer is 1,2,2,6,6-pentamethylpiperidine (stabilizer compound 31).

Secondary and tertiary amines can also be cyclic amines represented by the three and four membered rings chemical formulae (IV) and (V), respectively:

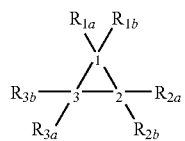

(IV)

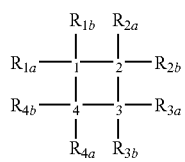

(V)

wherein, for the three-membered ring of formula (IV), at least one atom and no more than two atoms at positions 1-3 are nitrogen, the ring can contain an oxygen, phosphorous or sulfur heteroatom, and the remaining ring atoms are carbon. For the four-membered ring of formula (V), at least one atom and no more than two atoms at any one of positions 1-4 are nitrogen, the ring can contain an oxygen, phosphorous or sulfur heteroatom, and the remaining ring atoms are carbon. The rings of formulae (IV) or (V) can be unsaturated, partially unsaturated, or completely saturated. In the case of nitrogen ring atoms, only $R_{xa}$ (where x is any one of 1-3 for rings of formula (IV) and 1-4 for rings of formula (V)) is present at that atom, and where the ring is partially unsaturated or completely saturated, the nitrogen atom $R_{xa}$ substituent can represent a shared electron or electron pair. For carbon ring atoms, in the case of unsaturated rings, both $R_{xa}$ and $R^{xb}$ are present at that atom, and where the ring is partially unsaturated or completely saturated one of the carbon atom $R_{xa}$ or $R^{xb}$ substituent can represent a shared electron or electron pair.

The rings of formulae (IV) and (V) can be substituted or unsubstituted. A preferred three-membered rings is ethyleneimine. For rings of formula (IV), $R_{1a}$ through $R_{3b}$ are independently selected from a shared electron, electron pair, hydrogen, straight or branched chain alkyl, alkene or alkoxy having 1 to 8 carbon atoms, and cycloalkyl having 3 to 8 carbon atoms. For rings of formula (V), $R_{1a}$ through $R_{4b}$ are independently selected from a shared electron, electron pair, hydrogen, straight or branched chain alkyl, alkene or alkoxy having 1 to 8 carbon atoms, and cycloalkyl having 3 to 8 carbon atoms.

In an alternative embodiment, formulae (II) to (IV) may include ring atoms other than carbon and nitrogen. Thus, for example, formulae (II) to (IV) may include an oxygen, phosphorous or sulfur heteroatom. In one embodiment, therefore, the heterocycle may be thiazole or oxazole.

In another embodiment, aminoborohydrides suitable for use as BTHF stabilizers are represented by formula (VI):

$$R_1R_2R_3NH_4B^-M^+ \quad (VI)$$

where $R_1$, $R_2$ and $R_3$ are independently selected from straight or branched chain alkyl, alkene or alkoxy having 1 to 8 carbon atoms, and cycloalkyl having 3 to 8 carbon atoms and M is a metal cation. Suitable metal cations include, for example, lithium, sodium and potassium. Aminoborohydrides of formula (VI) are known in the art. See for example U.S. Pat. No. 5,466,798 to Singaram, et al.

In another preferred embodiment, sulfides suitable for use as BTHF stabilizers are represented by sulfides of formula (VIIa) and sulfoxides of formula (VIIb):

$$SR_4R_5(VIIa); \quad S(O)R_4R_5 \quad (VIIb)$$

wherein $R_4$ and $R_5$ are independently straight or branched chain alkyl, alkene or alkoxy having from 1 to 8 carbon atoms. In one embodiment the alkoxy is of the formula $(CH_2CH_2O)_n$ where n is 1 to 3. Sulfides of formula (VIIa) are known in the art. See, for example, U.S. Pat. Nos. 5,504,240 and 5,567,849 to Brown, both of which are incorporated by reference. Sulfoxides of formula (VIIb) are known in the art. See, for example, U.S. Pat. No. 4,029,712 to Tsuchihashi et al., which is incorporated by reference.

Alternatively, $R_4$ and $R_5$ and the sulfur atom can form a substituted or unsubstituted heterocyclic ring structure containing from 3 to 8 atoms. One such preferred ring is thiophene. The heterocyclic ring can be substituted with one or more groups defined for $R_1$ above.

Representative sulfide stabilizers of formula (VIIa) are indicated in Table 2 below. Representative sulfoxide stabilizers of formula (VIIb) also have the substituents as indicated in Table 2.

TABLE 2

| Stabilizer | $R_4$ | $R_5$ |
|---|---|---|
| 32 | i-amyl | ethyl |
| 33 | i-amyl | methyl |
| 34 | i-amyl | t-butyl |
| 35 | i-amyl | i-amyl |
| 36 | 2-methoxyethyl | 2-methoxyethyl |
| 37 | 2-methoxyethyl | ethyl |
| 38 | t-butyl | ethyl |
| 39 | methyl | methyl |
| 40 | $(CH_2CH_2O)_2$ | ethyl |
| 41 | $(CH_2CH_2O)_2$ | t-butyl |
| 42 | $(CH_2CH_2O)_2$ | i-amyl |
| 43 | $(CH_2CH_2O)_3$ | ethyl |
| 44 | $(CH_2CH_2O)_3$ | t-butyl |
| 45 | $(CH_2CH_2O)_3$ | i-amyl |

In still another preferred embodiment, phosphines suitable for use as BTHF stabilizers are represented by formulae (VIII), (IX) and (X):

(VIII)

(IX)

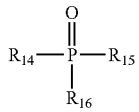
(X)

For the phosphine of formula (VII), $R_6$, $R_7$ and $R_8$ are independently selected from hydrogen, straight or branched chain alkyl or alkyne having from 1 to 14 carbon atoms, substituted or unsubstituted cycloalklyl having from 3 to 8 carbon atoms, and substituted or unsubstituted phenyl, provided, however, only one of $R_6$, $R_7$ and $R_8$ is hydrogen. Preferred cycloalkyls are cyclopentyl and cyclohexyl. Preferred substituted phenyls are xylyl (dimethylbenzene) and tolyl (methylbenzene).

Representative phosphine stabilizers of formula (VIII) are indicated in Table 3 below.

TABLE 3

| Stabilizer | $R_6$ | $R_7$ | $R_8$ |
|---|---|---|---|
| 46 | H | i-butyl | i-butyl |
| 47 | H | phenyl | phenyl |
| 48 | tetradecene-1 | phenyl | phenyl |
| 49 | H | ethyl | ethyl |
| 50 | tetradecene-1 | ethyl | ethyl |
| 51 | n-butyl | n-butyl | n-butyl |
| 52 | H | n-butyl | n-butyl |
| 53 | phenyl | phenyl | phenyl |
| 54 | xylyl | xylyl | xylyl |
| 55 | tolyl | tolyl | tolyl |
| 56 | allyl | allyl | i-butyl |
| 57 | allyl | allyl | cyclohexyl |
| 58 | allyl | allyl | sec-butyl |
| 59 | allyl | allyl | hexyl |
| 60 | allyl | allyl | cyclopentyl |

For the phosphine of formula (IX), $R_9$, $R_{10}$, $R_{11}$, $R_{12}$ and $R_{13}$ are independently selected from hydrogen, straight or branched chain alkyl or alkyne having from 1 to 14 carbon atoms, substituted or unsubstituted cycloalklyl having from 3 to 8 carbon atoms, and substituted or unsubstituted phenyl. Only one or two of $R_9$, $R_{10}$, $R_{11}$, $R_{12}$ and $R_{13}$ can be hydrogen. Preferred cycloalkyls are cyclopentyl and cyclohexyl. Preferred substituted phenyls are xylyl and tolyl.

A representative phosphine stabilizer of formula (IX) is 1,1,3,3-tetramethylbutylphosphine (stabilizer compound 61).

For the phosphine oxides of formula (X), $R_{14}$, $R_{15}$ and $R_{16}$ are independently selected from hydrogen, straight or branched chain alkyl or alkyne having from 1 to 14 carbon atoms, substituted or unsubstituted cycloalklyl having from 3 to 8 carbon atoms, and substituted or unsubstituted phenyl. Only one of $R_6$, $R_7$ and $R_8$ can be hydrogen. Preferred cycloalkyls are cyclopentyl and cyclohexyl. Preferred substituted phenyls are xylyl and tolyl.

Representative phosphine oxide stabilizers of formula (X) have the substituents as indicated in Table 3 above except where $R_6$, $R_7$ and $R_8$ as indicated in that table are instead $R_{14}$, $R_{15}$ and $R_{16}$, respectively.

Alternatively, any two of $R_6$-$R_8$, $R_9$-$R_{13}$ or $R_{14}$-$R_{16}$ and the phosphorus atom can form a substituted or unsubstituted heterocyclic phosphine ring structure containing from 3 to 8 atoms. Phosphine rings are known in the art. See, for example, U.S. Pat. Nos. 4,503,178 to Green and 6,545,183 B1 to Berens, both of which are incorporated by reference. The phosphine ring can be substituted with any of the groups defined for $R_1$ above.

Phosphines of formulae (VIII), (IX) and (X) are known in the art. See, for example, U.S. Pat. Nos. 4,008,282 to Townsend et al., 4,390,729 to Oswald, 5,100,854 to Maeda et al., 5,250,736 to Micklethwaite et al., 5,260,485 to Calbick et al. and 5,663,419 to Sugiya et al., all of which are incorporated by reference.

In yet another embodiment, the stabilizer is a borate. Without being bound to any particular, it has been proposed that these stabilizers react/exchange with borane according to the following reaction scheme:

wherein free borane ($BH_3$) is scavenged thereby stabilizing BTHF assay and increasing the SADT temperature. The borate stabilizer, for example, may be represented by formulae (XI) or (XII):

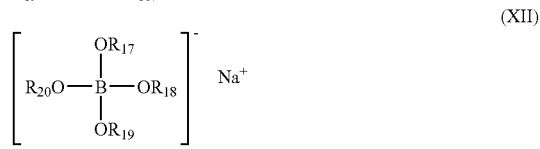

wherein $R_{17}$, $R_{18}$, $R_{19}$ and $R_{20}$ are independently selected from an straight or branched chain alkyl or alkenyl having from 1 to 8 carbon atoms. A sodium counterion is indicated for formula (XII), but any suitable metallic counterion, such as potassium, is suitable for use. A representative borate-based stabilizer of formula (XI) is $B(OCH_2CH_2CH_2CH_3)_3$ (stabilizer compound 62).

As previously noted, the stabilizers of the present invention may optionally be supported on or in a polymer matrix, or on or in an inert carrier such as titanium dioxide, silicone dioxide, alumina, carbon or zeolite. Advantageously, a polymer matrix possesses both barrier properties and structural integrity. Suitable polymers include, for example, polyolefin, polyvinyl chloride, nitrile, polyethylene terephthalate (e.g., Mylar® or "PET"), polyurethane, polystyrene, polytetrafluoroethylene (e.g., Teflon® or "PTFE"), silicone rubber and polyvinylidene chloride. The stabilizer can bound to the polymer or carrier at any one of the positions indicated by $R_1$ through $R_{20}$ and $R_{1a}$ through $R_{6b}$, or at a substituted group designated by any of $R_1$ through $R_{20}$ and $R_{1a}$ through $R_{6b}$. Alternatively, any of the stabilizers of the present invention can be included, such as by adsorption or absorption, within the matrix of a porous polymer or inert carrier.

The stabilizer is useful for the storage and transportation of BTHF solutions, as well as for the return of substantially empty BTHF containers for refilling. The stabilizer can be included in the BTHF solution in a variety of ways. For instance, first, a stabilizer that is essentially soluble in or miscible with THF can be added to the BTHF solution. Second, a substantially insoluble stabilizer or stabilizer matrix can be used. In the second case, the stabilizer can be isolated within the BTHF storage container to prevent the stabilizer from settling out of solution. Suitable isolation methods include, for example: coating the inside of the storage container or a container insert with the stabilizer; placing the stabilizer within a storage container insert barrier device that is permeable to gas and liquid, but is essentially impermeable to the insoluble stabilizer, such as, for example a perforated sphere or pipe, shaped or formed screen, or micro-perforated sealed bag. Third, stabilizers can be isolated from the storage container as described above to enable a time-release addition to the BTHF solution. Advantageously, container stabilizer inserts facilitate ease of introduction and removal of the stabilizer to and from the storage container. It is noted that the container stabilizer isolation methods are not limited to substantially insoluble and sparingly soluble stabilizers, but can also be used to contain essentially soluble or miscible stabilizers thereby achieving the benefits of time release and ease of introduction to the BTHF solution.

Storage vessel geometry can affect the rate of decomposition of both stabilized and unstabilized BTHF solutions. In particular, BTHF decomposition rate has been found to vary positively, and linearly, with the surface area of the BTHF solution exposed to the container vessel void volume. For containers of similar volume, tall vertical vessels having reduced diameter are preferred over shorter vessels having a greater diameter. Therefore, a storage vessel having dimensions selected to minimize the contained BTHF solution surface area to volume ratio are preferred over vessels of similar volume but having dimensions that yield a higher surface area to volume ratio. Moreover, it is preferred to store both stabilized and unstabilized BTHF solutions in vertical vessels rather than horizontal vessels because the surface area interface between the BTHF solution and the vessel gaseous void volume is minimized.

EXAMPLES

The following examples will illustrate the various features of the present invention.

Example 1

Figure 2:
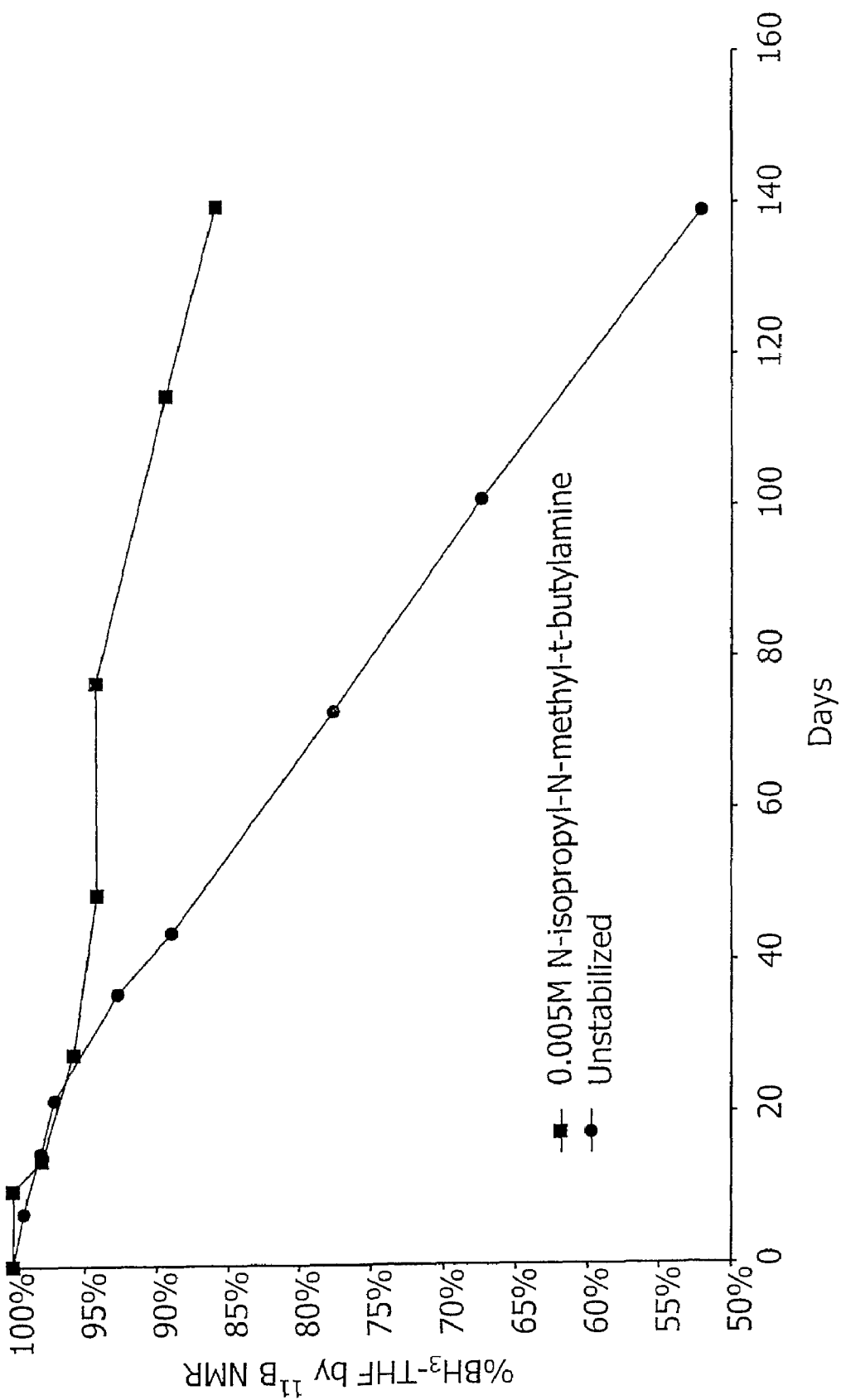
FIG. 2 is a graph of the mole percent borane-THF remaining (by ¹¹B NMR) in solution versus time in days for unstabilized and stabilized 1 mole per liter borane-THF solutions held at a temperature of 22° C.

A stock solution of BTHF was prepared and stored in a cooler. An aliquot was diluted to a 1.0 molar solution for an individual study (except where other concentrations are indicated). Selected stabilizers at the indicated concentrations were added and the resulting test solutions were sealed in NMR tubes. The tubes were heated to 50° C. and maintained at that temperature during the course of the experiment. BTHF assay was determined and reported at 24, 48 and 72 hours by $^{11}$B NMR. Where indicated, a 1.5 molar solution of BTHF obtained by diluting a stock solution aliquot, was evaluated for stability. The results, reported as percent BTHF-complex remaining in solution, are indicated in Table 4 below. FIG. 1 is a graph of the mole percent borane-THF remaining in solution versus time in hours for an unstabilized 1 mole per liter borane-THF solution and 1 mole per liter BTHF solutions stabilized with 0.005 moles per liter of NaBH$_4$ and stabilizer 15, respectively, held at a temperature of 50° C. FIG. 2 is a graph of the mole percent borane-THF remaining in solution versus time in days for an unstabilized 1 mole per liter borane-THF solution and 1 mole per liter BTHF solutions stabilized with 0.005 moles per liter of NaBH$_4$ and stabilizer 15, respectively, held at a temperature of 22° C.

TABLE 4

| Description | 24 hours | 48 hours | 72 hours |
|---|---|---|---|
| unstabilized 1.0M BTHF [a] | 82% [b] | 59% | 39% |
| unstabilized 1.5M BTHF | 71% | 38% | 19% |
| <0.005M NaBH$_4$ in 1.0M BTHF | 81% | 55% | 36% |
| 0.005M NaBH$_4$ in 1.0M BTHF [a] | 90% | 66% | 45% |
| 0.01M NaBH$_4$ in 1.0M BTHF | 91% | 69% | 47% |
| 0.005M LiBH$_4$ in 1.0M BTHF | 89% | 64% | 43% |
| 0.005M KBH$_4$ in 1.0M BTHF | 84% | 59% | 40% |
| 0.005M Stabilizer 6 in 1.0M BTHF | 83% | 65% | 48% |
| 0.005M Stabilizer 8 in 1.0M BTHF | 85% | 65% | 49% |
| 0.01M Stabilizer 8 in 1.0M BTHF | 86% [b] | 70% | 52% |
| 0.005M Stabilizer 15 in 1.0M BTHF [a] | 89% | 79% | 67% |
| 0.01M Stabilizer 15 in 1.0M BTHF | 92% | 77% | 72% |
| 0.025M Stabilizer 15 in 1.0M BTHF [a] | 87% | 74% | 61% |
| 0.01M Stabilizer 15 in 1.5M BTHF | 87% | 68% | 49% |
| 0.005M Stabilizer 16 in 1.0M BTHF | 83% | 59% | 43% |
| 0.005M Stabilizer 22 in 1.0M BTHF | 88% | 73% | 59% |
| 0.005M Stabilizer 25 in 1.0M BTHF | 85% | 65% | 49% |
| 0.005M Stabilizer 29 in 1.0M BTHF | 81% [b] | 55% | 36% |
| 0.01M Stabilizer 29 in 1.0M BTHF | 83% | 58% | 39% |
| 0.005M Stabilizer 31 in 1.0M BTHF [a] | 92% | 78% | 64% |
| 0.01M Stabilizer 31 in 1.5M BTHF | 85% | 63% | 45% |
| 0.005M Stabilizer 39 in 1.0M BTHF | 83% | 57% | 37% |
| 0.005M Stabilizer 62 in 1.0M BTHF | 82% | 57% | 39% |
| 0.005M pyridine-SiO$_2$ in 1.0M BTHF | 81% | 58% | 39% |

[a] Results are an average of multiple experiments
[b] Results are an estimation from 20 hours Stabilizers 6, 8, 15, 22, 25 and 31 showed increased stabilization of BTHF solution when compared to unstabilized BTHF. Stabilizers 6, 8 and 25 showed approximately equivalent stabilization as BTHF solution stabilized with NaBH$_4$. Stabilizers 15, 22 and 31 showed increased stabilization of BTHF solution when compared to BTHF solution stabilized with NaBH$_4$.

Using larger sample sizes of the stabilized solutions of Example 1, final active hydride content was determined by hydrolyzing the solution and measuring the hydrogen evolved according to the method of H. C. Brown, Organic Synthesis via Boranes Vol. 1 page 214 (1975), incorporated herein by reference. BTHF assay as measured by $^{11}$B NMR directly correlated to the active hydride content as measured by the method of H. C. Brown.

Example 2

To further quantify the stabilization effect, selected samples were subjected to thermal decomposition tests. Those tests were performed on representative samples of prepared solutions using Accelerating Rate Calorimetry. The testing apparatus comprised a nitrogen flushed Hastelloy C sphere that was charged with 5 grams of the solution. The solution was heated to 350° C. in a procedure wherein heating was done in 5° C. increments with a 15 minute wait after each heating increment. After the desired reaction time was reached, the apparatus was cooled to room temperature. The thermal and pressure data was then evaluated. The results are reported in Table 5 with the stabilizer concentration in each test being 0.005 moles per liter; [BTHF] being the concentration of the THF-borane complex in moles per liter (M); the reaction onset temperature (Onset) and reaction final temperature (Final) reported in ° C.; and the heat of reaction (ΔH) reported in Joules per gram (J/g).

TABLE 5

| Stabilizer | [BTHF] | Onset | Final | ΔH |
|---|---|---|---|---|
| none | 1.0 | 66.2 | 184.5 | 358.7 |
| none | 1.5 | 55.8 | 180.3 | 379.0 |
| NaBH$_4$ | 1.0 | 71.2 | 199.5 | 379.9 |
| NaBH$_4$ | 2.0 | 50.8 | 216.6 | 470.5 |
| Stabilizer 15 | 1.0 | 71.7 | 182.1 | 334.4 |
| Stabilizer 15 | 1.5 | 61.5 | 337.6 | 818.3 |
| Stabilizer 31 | 1.0 | 76.8 | 141.0 | 192.8 |
| Stabilizer 31 | 1.5 | 66.3 | 313.7 | 734.4 |

This experiment indicates that stabilized BTHF solutions show higher onset temperature than do unstabilized solutions.

Example 3

The effect of surface area ("SA") and the SA to volume ratio on the thermal decomposition of a 1 mole per liter solution of BTHF in THF containing 0.005 moles per liter of a stabilizer was evaluated. A given volume of the stabilized solution was charged to a glass vessel in a high-pressure glass 1 L autoclave or high pressure NMR tube. The sample was heated for 72 hours and then cooled to room temperature. Using both gas evolution measurement and $^{11}$B NMR, material from the cooled sample was analyzed for BTHF concentration with the results reported in moles per liter. The results are reported in Table 6 below with "Temp" indicating the reaction temperature and "Rate" indicating the BTHF molar decomposition rate in moles per hour.

TABLE 6

| Stabilizer | SA | SA/volume | Temp | [BTHF] | Rate |
|---|---|---|---|---|---|
| None | 13 mm$^2$ | 25.0 mm$^2$/mL | 50° C. | 0.39 | 0.85 |
| NaBH$_4$ | 13 mm$^2$ | 25.0 mm$^2$/mL | 50° C. | 0.45 | 0.76 |
| 15 | 13 mm$^2$ | 25.0 mm$^2$/mL | 50° C. | 0.67 | 0.46 |
| 15 | 800 mm$^2$ | 32.2 mm$^2$/mL | 50° C. | 0.53 | 0.62 |
| 15 | 1900 mm$^2$ | 75.4 mm$^2$/mL | 51° C. | 0.40 | 0.79 |

The data indicate that there is a linear correlation between BTHF surface area and stability effect expressed as moles of BTHF complex decomposed per hour. In particular, when a sample having a SA of 13 mm$^2$ was heated at 50° C., the 1M BTHF stabilized with 0.005M stabilizer 15 showed 67% of the active product remaining in solution after 72 hours, where as the unstabilized and 0.005M NaBH$_4$ stabilized 1M BTHF showed only 39% and 45%, respectively. However, when the solution surface area was increased to 1900 mm$^2$, 1M BTHF stabilized with 0.005M stabilizer 15 showed 40% of BTHF remaining in solution after heating for 72 hours at 50° C.

Example 4

Stabilized BTHF complex solutions were subjected to testing to determine if those solutions were acceptable for shipping under the UN Recommendations on the Transportation of Dangerous Goods H.2 Test (i.e., Adiabatic Storage Test). That test quantifies the magnitude of any exothermic activity and gas generation in a chemical system under the adiabatic conditions typically encountered during the manufacture or shipping of dangerous goods.

A low heat loss 1 dm$^3$ stainless steel Dewar flask, fitted with a flanged lid and equipped with an agitator, a temperature probe, thermo coaxial heater, reagent addition port, and having connections to a pressure sensor or gas measurement equipment, was used. The heat capacity of such a vessel is typically about 10% of that of the reaction mass, and the rate of heat loss is similar to that exhibited by a 5 m$^3$ vessel having natural cooling. In order to provide a heat loss environment more closely related to large vessels (about 20 m$^3$), the calorimeter was placed in an adiabatic shield in which the temperature of the vessel surroundings is controlled to ensure that there is no heat flow through the calorimeter walls.

In the test, 750 mL of a prepared 1 mole per liter BTHF complex solution containing 0.005 moles per liter of the indicated stabilizer was charged to the nitrogen-purged Dewar flask which was then placed in a fan-assisted oven installed in a blast enclosure. The flask was then heated to a fixed temperature and held for a period of time to monitor exothermic activity. Temperature changes of less than about 0.1 K·hr$^{-1}$ per hour correspond to a power change of greater than 0.1 W·dm$^{-3}$ and can therefore be measured. Normally, detection limits of 1 K·hr$^{-1}$ are employed for onset determination studies to account for the heat input due to, for example, agitation. The procedure was repeated until self-heating (i.e., an exotherm) was observed.

The critical ambient temperature and SADT for a given container volume was calculated according to the UN test protocol as follows:
(1) For each container size, the calculated rates of heat generation per unit mass (plotted on the ordinate, or y-axis) as a function of temperature (plotted on the abscissa, or x-axis) were plotted on a graph having linear scales. A heat generation curve for each container size having the best fit was drawn through the plotted points;
(2) A straight line was drawn tangential to the each generation curve; and
(3) The intersection of that straight line and the abscissa is the critical ambient temperature, i.e., the highest temperature at which the packaged material does not show self-accelerating decomposition.

SADT is the critical ambient temperature rounded up to the next higher multiple of 5° C. Material having a SADT of 50° C. or higher (a critical ambient temperature of 45° C. or higher) is acceptable for shipping under UN Recommendations on the Transportation of Dangerous Goods test.

Figure 3:
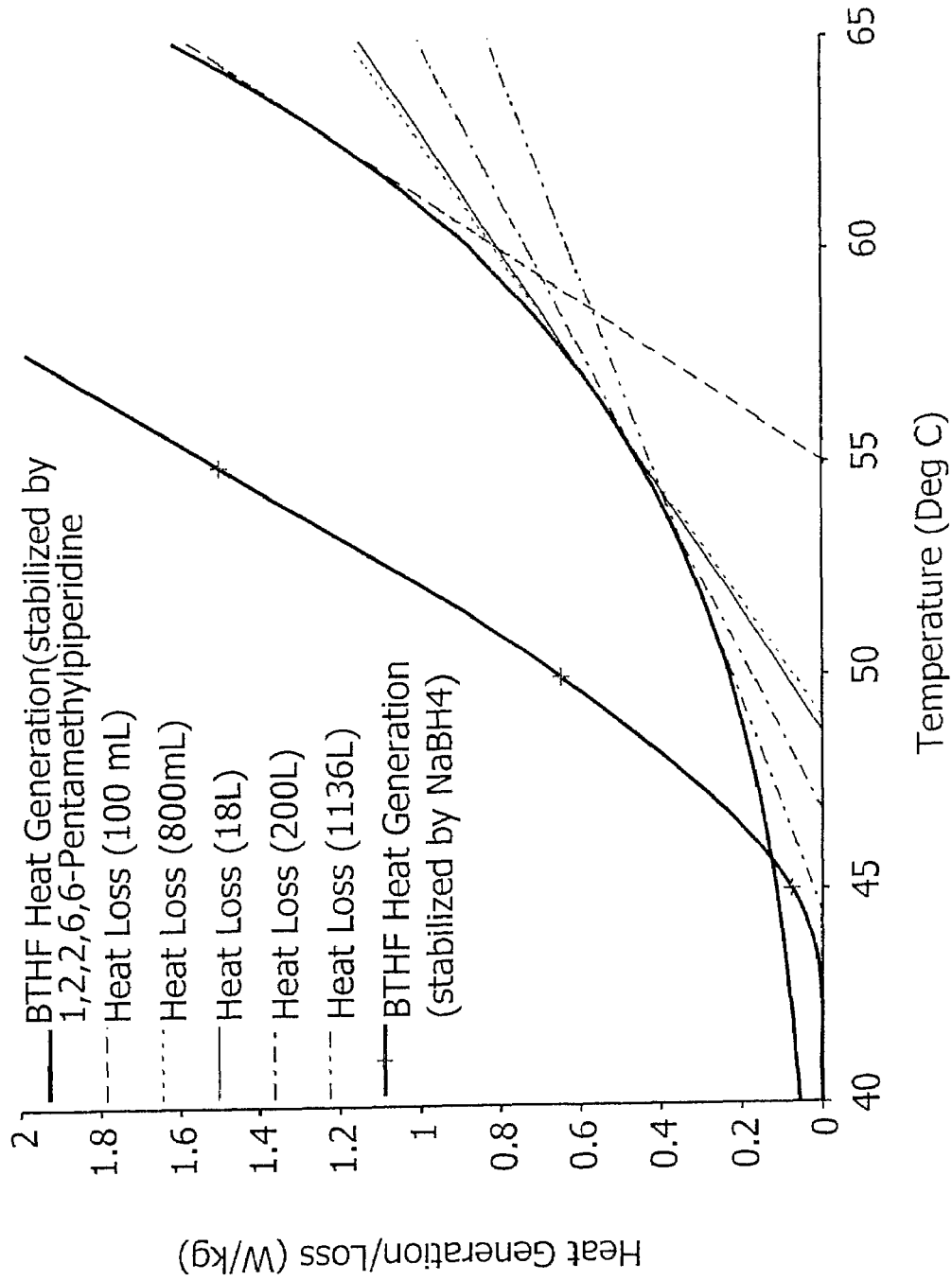
FIG. 3 is a graph of heat generation/loss versus temperature for various sized containers containing a 1M borane-THF solution stabilized with 1,2,2,6,6-Pentamethylpiperidine or NaBH₄ (comparative). The tangential lines represent the heat loss pattern for the containers, with the intersection of those lines with the X-axis representing the critical ambient temperature of the containers.
Figure 4:
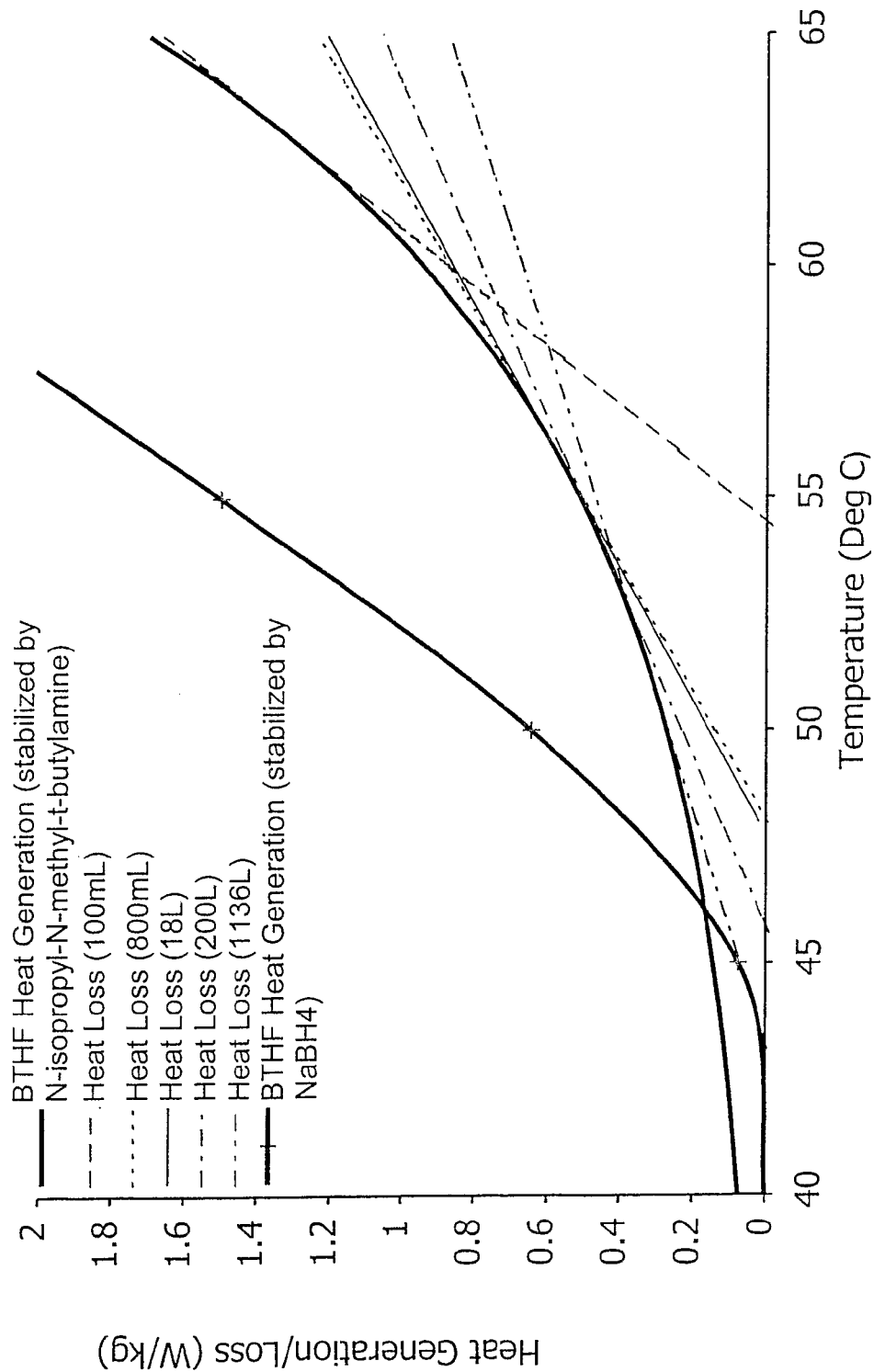
FIG. 4 is a graph of heat generation/loss versus temperature for various sized containers containing a 1M borane-THF solution stabilized with N-isopropyl-N-methyl-t-butylamine or NaBH₄ (comparative). The tangential lines represent the heat loss pattern for the containers, with the intersection of those lines with the X-axis representing the critical ambient temperature of the containers.

The critical ambient temperature and SADT data was collected and analyzed and is reported FIGS. 3 and 4, and in Table 7 below for various container sizes.

TABLE 7

| Stabilizer | 100 mL | 800 mL | 18 L | 200 L | 1136 L |
|---|---|---|---|---|---|
| | Critical Ambient Temperature (° C.) | | | | |
| NaBH$_4$ | 46.4 | 43.0 | 42.7 | 42.0 | 41.3 |
| 15 | 54.4 | 48.1 | 47.7 | 45.8 | 43.3 |
| 31 | 55.0 | 49.0 | 48.7 | 46.9 | 44.5 |
| | SADT (° C.) | | | | |
| NaBH$_4$ | 50 | 45 | 45 | 45 | 45 |
| 15 | 55 | 50 | 50 | 50 | 45 |
| 31 | 55 | 50 | 50 | 50 | 45 |

The data show that a 1 M amine-stabilized BTHF solution has a higher SADT temperature than does a 1 M NaBH$_4$-stabilized BTHF solution king it acceptable for shipping under the UN recommendations.

What is claimed is:

1. A composition containing a borane-tetrahydrofuran complex, tetrahydrofuran and a stabilizer wherein (i) the stabilizer is selected from the group consisting of amines, sulfides, phosphines, aminoborohydrides, borates, and combinations thereof, (ii) the concentration of the borane-tetrahydrofuran complex in the composition is at least about 0.5 moles per liter, and (iii) the molar ratio of the borane-tetrahydrofuran complex to the stabilizer is at least 10:1.

2. The composition of claim 1 wherein the molar ratio of the borane-tetrahydrofuran complex to the stabilizer is from about 10:1 to about 10000:1.

3. The composition of claim 1 wherein the concentration of the borane-tetrahydrofuran complex is about 0.5 moles per liter to about 2.5 moles per liter.

4. The composition of claim 1 wherein the amine stabilizer is of formula (Ia), formula (Ib) or formula (Ic):

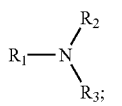  (Ia)

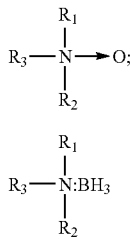  (Ib)

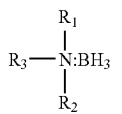  (Ic)

wherein
R$_1$ is selected from hydrogen, phenyl, straight or branched chain alkyl, alkene or alkoxy having 1 to 8 carbon atoms, cycloalkyl having 3 to 8 carbon atoms, and silyl tri-substituted with substituents independently selected from hydrogen, phenyl, and straight or branched chain alkyl, alkene or alkoxy having 1 to 8 carbon atoms, and
R$_2$ and R$_3$ are independently selected from phenyl, straight or branched chain alkyl, alkene or alkoxy having 1 to 8 carbon atoms, cylcoalkyl having 3 to 8 carbon atoms, and silyl tri-substituted with substituents independently selected from hydrogen, phenyl, and straight and branched chain alkyl, alkene or alkoxy having 1 to 8 carbon atoms.

5. The composition of claim 4 wherein
R$_1$ is selected from the group consisting of hydrogen, methyl, ethyl, n-propyl, i-propyl, n-butyl, i-butyl, t-butyl, sec-butyl, t-octyl, ethyl ether, ethyl methyl ether, methylallyl, phenyl and trimethylsilyl, and
R$_2$ and R$_3$ are independently selected from the group consisting of methyl, ethyl, n-propyl, i-propyl, n-butyl, i-butyl, t-butyl, sec-butyl, t-octyl, ethyl ether, ethyl methyl ether, methylallyl, phenyl and trimethylsilyl.

6. The composition of claim 1 wherein the amine stabilizer is a metal amide of formula (Id):

  (Id)

wherein
R$_1$ and R$_2$ are independently selected from hydrogen, phenyl, straight or branched chain alkyl, alkene or alkoxy having 1 to 8 carbon atoms, cycloalkyl having 3 to 8 carbon atoms, and silyl tri-substituted with substituents independently selected from hydrogen, phenyl, and straight or branched chain alkyl, alkene or alkoxy having 1 to 8 carbon atoms, and
M$^+$ is a metal counterion.

7. The composition of claim 6 wherein
R$_1$ and R$_2$ are independently selected from the group consisting of methyl, ethyl, n-propyl, i-propyl, n-butyl, i-butyl, t-butyl, sec-butyl, t-octyl, ethyl ether, ethyl methyl ether, methylallyl, phenyl and trimethylsilyl, and
M$^+$ is selected from sodium, potassium and lithium.

8. The composition of claim 1 wherein the amine stabilizer is a heterocyclic ring of formula (II):

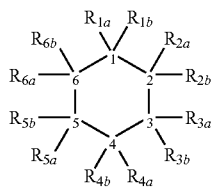  (II)

wherein
the heterocyclic ring contains heteroatoms selected from nitrogen, oxygen, phosphorous and sulfur,
at least one atom and no more than three atoms at ring positions 1-6 are nitrogen, no more than one heteroatom is oxygen, phosphorous or sulfur, and the remaining atoms at ring positions 1-6 are carbon,
the ring is unsaturated, partially unsaturated, or completely saturated,
nitrogen ring atoms each have one substituted group represented by R$_{1a}$, R$_{2a}$, R$_{3a}$, R$_{4a}$, R$_{5a}$ or R$_{6a}$, wherein substituted groups represented by R$_{1b}$, R$_{2b}$, R$_{3b}$, R$_{4b}$, R$_{5b}$ or R$_{6b}$ are not present, and wherein R$_{1a}$, R$_{2a}$, R$_{3a}$, R$_{4a}$, R$_{5a}$ and R$_{6a}$ are independently selected from a shared electron, electron pair, hydrogen, straight or branched chain alkyl, alkene or alkoxy having 1 to 8 carbon atoms, and cycloalkyl having 3 to 8 carbon atoms, and
carbon ring atoms each have two substituted groups represented by the substituted group pairs R$_{1a}$ and R$_{1b}$, R$_{2a}$ and R$_{2b}$, R$_{3a}$ and R$_{3b}$, R$_{4a}$ and R$_{4b}$, R$_{5a}$ and R$_{5b}$ or R$_{6a}$ and R$_{6b}$, wherein R$_{1a}$, R$_{1b}$, R$_{2a}$, R$_{2b}$, R$_{3a}$, R$_{3b}$, R$_{4a}$, R$_{4b}$, R$_{5a}$, R$_{5b}$, R$_{6a}$ and R$_{6b}$ are independently selected from a shared electron, electron pair, hydrogen, straight or branched chain alkyl, alkene or alkoxy having 1 to 8 carbon atoms, and cycloalkyl having 3 to 8 carbon atoms.

9. The composition of claim 8 wherein the ring of formula (II) is selected from substituted or unsubstituted piperidine, piperazine, pyridine, pyrazine, pyridazine and pyrimidine.

10. The composition of claim 1 wherein the amine stabilizer is a heterocyclic ring of formula (III):

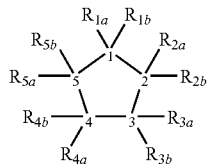  (III)

wherein
the heterocyclic ring contains heteroatoms selected from nitrogen, oxygen, phosphorous and sulfur,
at least one atom and no more than three atoms at ring positions 1-5 are nitrogen, no more than one heteroatom is oxygen, phosphorous or sulfur, and the remaining atoms at ring positions 1-5 are carbon, the ring is unsaturated, partially unsaturated, or completely saturated, nitrogen ring atoms each have one substituted group represented by $R_{1a}$, $R_{2a}$, $R_{3a}$, $R_{4a}$ or $R_{5a}$, wherein the substituted groups represented by $R_{1b}$, $R_{2b}$, $R_{3b}$, $R_{4b}$ or $R_{5b}$ are not present, and wherein $R_{1a}$, $R_{2a}$, $R_{3a}$, $R_{4a}$ and $R_{5a}$ are independently selected from a shared electron, electron pair, hydrogen, straight or branched chain alkyl or alkene having 1 to 8 carbon atoms, alkoxy having 1 to 5 carbon atoms, and cycloalkyl having 3 to 8 carbon atoms, and carbon ring atoms each have two substituted groups represented by the substituted group pairs $R_{1a}$ and $R_{1b}$, $R_{2a}$ and $R_{2b}$, $R_{3a}$ and $R_{3b}$, $R_{4a}$ and $R_{4b}$ or $R_{5a}$ and $R_{5b}$, and $R_{1a}$, $R_{1b}$, $R_{2a}$, $R_{2b}$, $R_{3a}$, $R_{3b}$, $R_{4a}$, $R_{4b}$, $R_{5a}$ and $R_{5b}$ are independently selected from a shared electron, electron pair, hydrogen, straight or branched chain alkyl, alkene or alkoxy having 1 to 8 carbon atoms, and cycloalkyl having 3 to 8 carbon atoms.

11. The composition of claim 10 wherein the ring of formula (III) is selected from substituted or unsubstituted 1H-Pyrrole, pyrrolidine, 3-pyrroline, imidazole, pyrazole, 2-pyrazoline and triazole.

12. The composition of claim 8 or claim 10 wherein the heterocyclic ring contains one nitrogen heteroatom and a sulfur or oxygen heteroatom.

13. The composition of claim 1 wherein the aminoborohydride is of formula (VI):

$$R_1R_2R_3\text{---}NH_4B^-M^+ \quad (VI)$$

wherein $R_1$, $R_2$ and $R_3$ are independently selected from straight or branched chain alkyl, alkene or alkoxy having 1 to 8 carbon atoms, and cycloalkyl having 3 to 8 carbon atoms, and M is a metal cation selected from lithium, sodium and potassium.

14. The composition of claim 1 wherein the phosphine is of formula (VIII):

(VIII)

wherein $R_6$, is selected from hydrogen, straight or branched chain alkyl, alkene or alkyne having from 1 to 14 carbon atoms, substituted or unsubstituted cycloalklyl having from 3 to 8 carbon atoms, and substituted or unsubstituted phenyl, and $R_7$ and $R_8$ are independently selected from straight or branched chain alkyl, alkene or alkyne having from 1 to 14 carbon atoms, substituted or unsubstituted cycloalkyl having from 3 to 8 carbon atoms, and substituted or unsubstituted phenyl.

15. The composition of claim 14 wherein the cycloalkyl is selected from cyclopentyl and cyclohexyl, and the phenyl is selected from xylyl and tolyl.

16. The composition of claim 14 wherein any two of $R_6$-$R_8$ and the phosphorus atom form a substituted or unsubstituted heterocyclic phosphine ring structure containing from 3 to 8 atoms.

17. The composition of claim 1 wherein the borate is of formulae (XI) or (XII):

(XI)

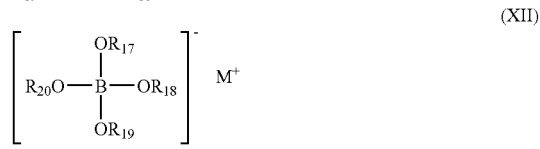

(XII)

wherein $R_{17}$, $R_{18}$, $R_{19}$ and $R_{20}$ are independently selected from an alkyl or alkenyl having from $_1$ to $_8$ carbon atoms, and $M^+$ is a metal counterion.

18. The composition of claim 1 wherein the stabilizer is supported on at least a portion of the surface of a polymer matrix or an inert carrier, in at least a portion of an internal matrix or pores of the polymer matrix or an inert carrier, or on at least a portion of the surface and at least a portion of the internal matrix of a polymer matrix or an inert carrier wherein the polymer matrix or inert carrier are immersed in the composition.

19. The composition of claim 18 wherein the inert carrier is selected from titanium dioxide, silicone dioxide, alumina, carbon and zeolite.

20. The composition of claim 18 wherein the polymer is selected from polyolefin, polyvinyl chloride, nitrile, polyethylene terephthalate, polyurethane, polystyrene, polytetrafluoroethylene, silicone rubber and polyvinylidene chloride.

21. The composition of claim 1 wherein the composition is a solution.

22. A method of storing a composition containing at least about 0.5 moles per liter of a borane-tetrahydrofuran complex in a solvent system comprising tetrahydrofuran, the method comprising sealing a container having a storage volume of at least 0.10 liters, the sealed container containing a liquid in the storage volume, the liquid comprising tetrahydrofuran, a borane-tetrhydrofuran complex, and a stabilizer selected from the group consisting of amines, sulfides, phosphines, aminoborohydrides, borates, and combinations thereof wherein the molar ratio of the borane-tetrahydrofuran complex to the stabilizer is at least 10:1.

23. The method of claim 22 wherein the molar ratio of the borane-tetrahydrofuran complex to the stabilizer is from about 10:1 to about 10000:1.

24. The method of claim 22 wherein the concentration of the borane-tetrahydrofuran complex is about 0.5 moles per liter to about 2.5 moles per liter.

* * * * *